(12) United States Patent
Mercep et al.

(10) Patent No.: US 7,435,834 B2
(45) Date of Patent: Oct. 14, 2008

(54) 2-THIA-DIBENZOAZULENES AS INHIBITORS OF TUMOUR NECROSIS FACTOR PRODUCTION AND INTERMEDIATES FOR THE PREPARATION THEREOF

(75) Inventors: Mladen Mercep, Zagreb (HR); Milan Mesic, Zagreb (HR); Dijana Pesic, Sibenik (HR); Ivana Ozimec, Trnovec (HR)

(73) Assignee: GlaxoSmithKline Istrazivacki Center Zagreb D.O.O., Zagreb (HR)

( * ) Notice: Subject to any disclaimer, the term of this patent is extended or adjusted under 35 U.S.C. 154(b) by 451 days.

(21) Appl. No.: 10/510,866

(22) PCT Filed: Apr. 9, 2003

(86) PCT No.: PCT/HR03/00016

§ 371 (c)(1),
(2), (4) Date: Feb. 24, 2005

(87) PCT Pub. No.: WO03/084962

PCT Pub. Date: Oct. 16, 2003

(65) Prior Publication Data

US 2005/0182126 A1     Aug. 18, 2005

(30) Foreign Application Priority Data

Apr. 10, 2002 (HR) .................. P 20020305 A

(51) Int. Cl.
*A61K 31/381* (2006.01)
*C07D 495/04* (2006.01)

(52) U.S. Cl. .................. 549/42; 514/439; 514/443
(58) Field of Classification Search .......... 549/42
See application file for complete search history.

(56) References Cited

U.S. PATENT DOCUMENTS

| 3,711,489 A | 1/1973 | Lombardino |
| 4,145,434 A | 3/1979 | Van Der Burg |
| 4,198,421 A | 4/1980 | Cherkofsky et al. |
| 6,511,976 B1 | 1/2003 | Andres-Gil et al. |

FOREIGN PATENT DOCUMENTS

| CA | 967573 | 5/1975 |
| EP | 0063525 | 10/1982 |
| EP | 0 125 484 | 11/1984 |
| EP | 0 357 126 | 3/1990 |
| EP | 0 372 455 | 6/1990 |
| HR | 20000310 | 2/2002 |
| WO | WO 96/14320 | 5/1996 |
| WO | WO 96/14321 | 5/1996 |
| WO | WO 97/38991 | 10/1997 |
| WO | WO 99/19317 | 4/1999 |
| WO | WO-01/87890 | 11/2001 |
| WO | WO 01/87890 A1 | 11/2001 |
| WO | WO 2003/084962 | 10/2003 |
| WO | WO 2005/049020 | 6/2005 |
| WO | WO 2005/072728 | 8/2005 |

OTHER PUBLICATIONS

Gansser C. et al. "Determination de l'activite radioprotectrice d'analogues de l'imipramine" Ann. Pharm. (1984), 41, 465-471.
Pfeffer et al., Mice Deficient for the 55 kd Tumor Necrosis Factor Receptor Are Resistant to Endotoxic Shock, yet Succumb to L. monocytogenes Infection, Cell, 1993, 73:457-467.
Elliott et al., Randomoised double-blind comparison of chimeric monoclonal antibody to tumor necrosis factor alpha (cA2) versus placebo in rheumatoid arthritis, The Lancet, 1994, 344:1105-1110.
Keffer et al., Transgenic mice expressing human tumour necrosis factor: a predictive genetic model of arthritis, EMBO J., 1991, 10:4025-4031.
Carswell et al., An endotoxin-induced serum factor that causes necrosis of tumors, Proc. Natl. Acad. Sci. U.S.A., 1975, 72:3666-3670.
Mori et al., Attenuation of Collagen-Induced Arthritis in 55-kDa TNF Receptor Type 1 (TNFR1)-IgG1-Treated and TNFR1-Deficient Mice, J. Immunol., 1996, 157:3178-3182.
Georgopoulos et al., Transmembrane TNF Is Sufficient To Induce Localized Tissue Toxicity and Chronic Inflammatory Arthritis In Transgenic Mice, J. Imflamm., 1996, 46:86-97.
Dinarello et al., Interleukin-1, Rev. Infect Disease, 1984, 6(1):51-95.
Bresnihan et al., Treatment with Recombinant Human Interleukin-1 Receptor Antagonist (rhIL-1ra) in Rheumatoid Arthritis (RA); Results of a Randomized Double-Blind, Placebo-Controlled Multicenter trial, Arthrit. Rheum., 1996, 39:73.
Dinarello, An Update on Human Interleukin-1: From Molecular Biology to Clinical Relevance, J. Clinical Immunology, 1985, 5:287.
Van Assche and Rutgeerts, Anti-TNF agents in Chrohn's disease., Exp. Opin. Invest. Drugs, 2000, 9:103-111.
Lombardino, Synthesis of Some Novel Tetracyclic Imidazole Derivatives, J Heterocyclic Chem., 1974, 11:17-21.
Menozzi, omega-Dialkylaminoalkyl Ethers of Phenyl-(5-substituted 1-phenyl-1H-pyrazol-4-yl)methanols with Analgesic and Anti-inflammatory Activity, J. Heterocyclic Chem., 1997, 34:963-968.
Chadwick et al., Preparation of Thiophen Esters by the Hinsberg Reaction, J. Chem. Soc. Perkin Trans. 1, 1972, 2079-2081.
Leonard et al., The Influence of Steric Configuration on the Ultraviolet Absorption of "Fixed" Benzils, J. Am. Chem. Soc., 1955, 77:5078.
Overberger et al., Cyclic Sulfones. II. The Polymerization of Styrene on the Presence of 3,4-Diphenylthiophene-1-dioxide and 3,4-Di-(p-chlorophenyl)-thiophene-1-dioxide, J. Am. Chem. Soc., 1950, 72:4958-4961.
Badger et al., Pharmacological Profile of SB 203580, a Selective Inhibitor of Cytokine Suppressive Binding Protein/p38 Kinase, in Animal Models of Arthritis, Bone Resorption, Endotoxin Shock and Immune Function, J. Pharmac. Env. Therap., 1996, 279:1453-1461.
Fukawa et al., A Method for Evaluating Analgesic Agents in Rats, J. Pharmacol. Meth., 1980, 4:251-259.

(Continued)

*Primary Examiner*—Laura L. Stockton
(74) *Attorney, Agent, or Firm*—J. Scott Young

(57) ABSTRACT

The present invention relates to compounds of 2-thia-dibenzoazulene class, to their pharmacologically acceptable salts and solvates, to processes and intermediates for the preparation thereof as well as to their antiinflammatory effects, especially to the inhibition of tumour necrosis factor-α(TNF-α) production and the inhibition of interleukin-1 (IL-1) production as well as to their analgetic action.

14 Claims, No Drawings

OTHER PUBLICATIONS

Schweizer et al., Combined automated writhing/motility test for testing analgesics, Agents and Actions, 1988, 23:29-31.

Collier et al., The Abdominal Constriction Response and Its Suppression By Analgesic Drugs in the Mouse, Br. J. Pharmac. Chemother., 1968, 32:295-310.

Gansser et al., Determination de l'active radioprotrctrice d'analogues de l'imipramine, Ann. Pharm., 1983, 41(5):465-471.

Schulz et al., Synthese von 1, 3a,3, 12b-Tertrahydro-dibenzo[b,f]-pyrasolo[3,4-d]azepin-Derivaten, Z. Chem, 1988, 25: 181-182.

Funke et al., Physico-chemical Properties and Stability of trans-5-Chloro-2-methyl1-2-3, 3a, 12b-tetrahydro-1h-dibenz[2,3,:6,7]oxepino[4,5-c]pyrrolidine Maleate, Arzeim-Forsch., 1990, 40:536-539.

Bennett et al., Reaction of 5-Acety 1-10, didehydroi-5H-dibenz[b,f] azepine with Pyrrole, N-Methylpyrrole, Imadazolke and N-Methylimidazole: Cycloaddtion Versus Michael Addition, J. Heterocycl. Chem., 1994, 31: 293-296.

Bymaster F., et al. "New Approaches to Developing Antidepressants By Enhancing Monoaminergic Neurotransmission." Expert Opinion Investig. Drugs, 2003, 12, pp. 531-543.

Spampinato U. et al. "Role of Striata Serotonin 2A and Serotinin 2C Receptor Subtypes in the Control of In Vivo Dopamine Outflow in the Rat Striatum." J. Neurochemistry, 2000, vol. 74, pp. 693-701.

Monnet F.P., et al. "N-Methyl-D-Aspartate-Induced Neuronal Activation Is Selectively Modulated by o Receptors." European Journal of Pharmacology, 1990, vol. 179, pp. 441-445.

Claghorn J., et al. "N-Methyl-D-Aspartate-Induced In Antidepressant Agents." Progress in Drug Research Clinic Inc., 1996, vol. 46, pp. 243-262.

Sperling W. et al., "New Tetracyclic Antidepressants." Drugs Today, 1997, vol. 33, No. 2, pp. 95-102.

Andres J.I., et al. "R107500. A New 5-HT 2A/2C Antagonist With Potential Anxiolytic Profile." Drugs Fut., 2002, vol. 27, Suppl. A:C41.

Cid J.M., et al. "Synthesis Of 2-Aminomethyl-3, 3a, 8, 12." Drugs Fut., 2002, vol. 27, Suppl. A:P182.

Meert T.F., et al. "Psychopharmacology Of Ritanserin: Comparison With Chlordiazepoxide." Drug Development Research, 1989, vol. 18, pp. 119-144.

Niemegeers C.J.E., et al. "Interaction Of Drugs With Apomorphine, Tryptamine And Norepinephrine. A New "In Vivo" Approach: The ATN-Test In Rats." Arch. Int. Pharmacodyn., 1977, vol. 227, pp. 238-253.

Berge S.M., et al. "Pharmaceutical Salts." Journal of Pharmaceutical Sciences, 1997, vol. 66, pp. 1-20.

Thomson W., et al. Juvenile Idiopathic Arthritis Genetics - What's New? What's Next? Arthritis Research, 2002, vol. 4 and 5, pp. 302-306.

Wolf W.A., et al. "The Serotonin 5-HT 2C Receptor Is A Prominent Serotinin Receptor In Basel Ganglia: Evidence From Functional Studies On Serotonin-Mediated Phosphoinositide Hydrolysis." Journal of Neurochemistry, 1997, vol. 69, p. 1449.

Porsolt R.D., et al. "Behavioral Despair in Mice: A Primary Screening Test For Antidepressants." Arch. Int. Pharmacodyn., 1997, vol. 229, pp. 327-336.

Millam M.J., et al. "S18126 ({2-4-2,3-dihydrobenzol(1,4) dioxin-6-yl)piperazin-1-ylmethyl}), A Potent, Selective and Competitive Antagonist at Dopamine D4 Receptors: An in vitro and in vivo Comparison with L 745,870 (3-(4-(4-chlorophenyl)piperazin-1-yl)methyl-1H-pyrrolo[2,3b]pyridine) and raclopride." Journal of Pharmacology and Experimental Therapeutics, 1998, vol. 287, No. 1, pp. 167-186.

Bonhaus D.W., et al. "The Pharmacology and Distribution of Human 5-hydroxytrptamine 2B (5hT2B) Receptor Gene Products; Comparison With 5-HT2A and 5HT2C Receptors." British Journal of Pharmacology, 1995, vol. 115, pp. 622-628.

Saucier C., et al. "Identification of An Endogenous 5-Hydroxytryptamine 2A Receptor in NIH-3T3 Cells: Agonist-Induced Down-Regulation Inviolves Decreases in Receptor RNA and Number." Journal of Neurochemistry, 1997, vol. 68, No. 1, pp. 1998-2011.

Beers M.H., et al. "The Merck Manual of Diagnosis and Therapy, 17th edition." 1999, Merck Research Laboratories, p. 1474, column 1, paragraphy 4-1476, column 2, last paragraph.

PCT International Search Report for International No. PCT/HR2004/000042, Dated Jun. 23, 2006.

2-THIA-DIBENZOAZULENES AS INHIBITORS OF TUMOUR NECROSIS FACTOR PRODUCTION AND INTERMEDIATES FOR THE PREPARATION THEREOF

TECHNICAL FIELD

The present invention relates to compounds of 2-thia-dibenzoazulene class, to their pharmacologically acceptable salts and solvates, to processes and intermediates for the preparation thereof as well as to their antiinflammatory effects, especially to the inhibition of tumour necrosis factor-α (TNF-α) production and the inhibition of interleukin-1 (IL-1) production as well as to their analgetic action.

PRIOR ART

Hitherto, in the literature derivatives of 1-thia-dibenzoazulenes substituted in 2-position with methyl, methyl-ketone, nitro group or with carboxylic group derivatives (Cagniant PG, *C. R. Hebd. Sceances Acad. Sci.*, 1976, 283:683-686) have been described. Some 1,3-diaza-dibenzoazulene derivatives and salts thereof are known as a novel class of compounds having an antiinflammatory action (U.S. Pat. No. 3,711,489, U.S. Pat. No. 4,198,421 and CA 967,573). 1-Thia-dibenzoazulene derivatives having alkyloxy substituents in 2-position (WO 01/878990) also possess strong antiinflammatory action. However, according to our knowledge and to available literature data, compounds of 2-thia-dibenzoazulene structure in general have hitherto not been known and, thus, neither have been derivatives derived from this structure or their antiinflammatory action as inhibitors of TNF-α secretion and inhibitors of IL-1 secretion or their analgetic action.

In 1975 TNF-α was defined as a serum factor induced by endotoxin and causing tumour necrosis in vitro and in vivo (Carswell E A et al., *Proc. Natl. Acad. Sci. USA.*, 1975, 72:3666-3670). Besides an antitumour action, TNF-α also possesses numerous other biological actions important in the homeostasis of an organism and in pathophysiological conditions. The main sources of TNF-α are monocytes-macrophages, T-lymphocytes and mastocytes.

The discovery that anti-TNF-α antibodies (cA2) have an action in treating patients with rheumatoid arthritis (RA) (Elliott M et al., *Lancet,* 1994, 344:1105-1110) led to an increased interest in finding novel TNF-α inhibitors as possible potent drugs for RA. Rheumatoid arthritis is an autoimmune chronic inflammatory disease characterized by irreversible pathological changes in the joints. Besides in RA, TNF-α antagonists may also be used in numerous pathological conditions and diseases such as spondylitis, osteoarthritis, gout and other arthritic conditions, sepsis, septic shock, toxic shock syndrom, atopic dermatitis, contact dermatitis, psoriasis, glomerulonephritis, lupus erythematosus, scleroderma, asthma, cachexia, chronic obstructive lung disease, congestive cardiac arrest, insulin resistance, lung fibrosis, multiple sclerosis, Crohn's disease, ulcerative colitis, viral infections and AIDS.

Evidence for the biological importance of TNF-α was obtained by in vivo experiments in mice, in which mice gens for TNF-α or its receptor were inactivated. Such animals are resistant to collagen-induced arthritis (Mori L et al., *J. Immunol.*, 1996, 157:3178-3182) and to endotoxin-caused shock (Pfeffer K et al., *Cell,* 1993, 73:457-467). In animal experiments where TNF-α level was increased, a chronic inflammatory polyarthritis occured (Georgopoulos S et al., *J. Inflamm.*, 1996, 46:86-97; Keffer J et al., *EMBO J.*, 1991, 10:4025-4031) and its pathological picture was alleviated by inhibitors of TNF-α production. The treatment of such inflammatory and pathological conditions usually includes the application of non-steroid antiinflammatory drugs and, in more severe cases, gold salts, D-penicillinamine or methotrexate are administered. Said drugs act symptomatically, but they do not stop the pathological process. Novel approaches in the therapy of rheumatoid arthritis are based upon drugs such as tenidap, leflunomide, cyclosporin, FK-506 and upon biomolecules neutralizing the TNF-α action. At present there are commercially available etanercept (Enbrel, Immunex/Wyeth), a fusion protein of the soluble TNF-α receptor, and infliximab (Remicade, Centocor), a chimeric monoclonal human and mouse antibody. Besides in RA therapy, etanercept and infliximab are also registered for the therapy of Crohn's disease (*Exp. Opin. Invest. Drugs,* 2000, 9:103).

In RA therapy, besides inhibition of TNF-α secretion, also the inhibition of IL-1 secretion is very important since IL-1 is an important cytokin in cell regulation and immunoregulation as well as in pathophysiological conditions such as inflammation (Dinarello C A et al., *Rev. Infect. Disease,* 1984, 6:51). Well-known biological activities of IL-1 are: activation of T-cells, induction of elevated temperature, stimulation of secretion of prostaglandine or collagenase, chemotaxia of neutrophils and reduction of iron level in plasma (Dinarello C A, *J. Clinical Immunology,* 1985, 5:287). Two receptors to which IL-1 may bind are well-known: IL-1RI and IL-1RII. Whereas IL-1RI transfers a signal intracellularly, IL-1RII is situated on the cell surface and does not transfer a signal inside the cell. Since IL1-RII binds IL-1 as well as IL1-RI, it may act as a negative regulator of IL-1 action. Besides this mechanism of signal transfer regulation, another natural antagonist of IL-1 receptor (IL-1ra) is present in cells. This protein binds to IL-1RI but does not transfer any signal. However, its potency in stopping the signal transfer is not high and its concentration has to be 500 times higher than that of IL-1 in order to achieve a break in the signal transfer. Recombinant human IL-1ra (Amgen) was clinically tested (Bresnihan B et al., *Arthrit. Rheum.*, 1996, 39:73) and the obtained results indicated an improvement of the clinical picture in 472 RA patients over an placebo. These results indicate the importance of the inhibition of IL-1 action in treating diseases such as RA where IL-1 production is disturbed. Since there exists a synergistic action of TNF-α and IL-1, 2-thia-dibenzoazulenes may be used in treating conditions and diseases related to an enhanced secretion of TNF-α and IL-1.

Solution of Technical Problem

The present invention relates to 2-thia-dibenzoazulenes of the formula I

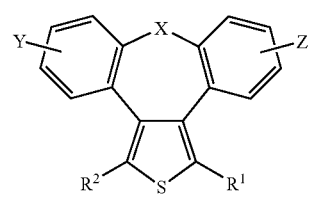

wherein

X may be $CH_2$ or a hetero atom such as O, S, S(=O), $S(=O)_2$, or $NR^a$, wherein $R^a$ is hydrogen or a protecting group;

Y and Z independently from each other denote one or more identical or different substituents linked to any available carbon atom, and may be halogen, $C_1$-$C_4$ alkyl, $C_2$-$C_4$ alkenyl, $C_2$-$C_4$ alkinyl, trifluoromethyl, halo-$C_1$-$C_4$ alkyl, hydroxy, $C_1$-$C_4$ alkoxy, trifluoromethoxy, $C_1$-$C_4$ alkanoyl, amino, amino-$C_1$-$C_4$ alkyl, $C_1$-$C_4$ alkylamino, N—($C_1$-$C_4$-alkyl)amino, N,N-di($C_1$-$C_4$-alkyl)amino, thiol, $C_1$-$C_4$ alkylthio, sulfonyl, $C_1$-$C_4$ alkylsulfonyl, sulfinyl, $C_1$-$C_4$ alkylsulfinyl, carboxy, $C_1$-$C_4$ alkoxycarbonyl, cyano, nitro;

$R^1$ may be hydrogen, halogen, an optionally substituted $C_1$-$C_7$ alkyl or $C_2$-$C_7$ alkenyl, $C_2$-$C_7$ alkinyl, an optionally substituted aryl or heteroaryl and a heterocycle, hydroxy, hydroxy-$C_2$-$C_7$ alkenyl, hydroxy-$C_2$-$C_7$ alkinyl, $C_1$-$C_7$ alkoxy, thiol, thio-$C_2$-$C_7$ alkenyl, thio-$C_2$-$C_7$ alkinyl, $C_1$-$C_7$ alkylthio, amino, N—($C_1$-$C_7$ alkyl)amino, N,N-di-($C_1$-$C_7$ alkyl)amino, $C_1$-$C_7$ alkylamino, amino-$C_2$-$C_7$ alkenyl, amino-$C_2$-$C_7$ alkinyl, amino-$C_1$-$C_7$ alkoxy, $C_1$-$C_7$ alkanoyl, aroyl, oxo-$C_1$-$C_7$ alkyl, $C_1$-$C_7$ alkanoyloxy, carboxy, an optionally substituted $C_1$-$C_7$ alkyloxycarbonyl or aryloxycarbonyl, carbamoyl, N—($C_1$-$C_7$-alkyl)carbamoyl, N,N-di($C_1$-$C_7$-alkyl)carbamoyl, cyano, cyano-$C_1$-$C_7$ alkyl, sulfonyl, $C_1$-$C_7$ alkylsulfonyl, sulfinyl, $C_1$-$C_7$ alkylsulfinyl, nitro, or a substituent of the formula II

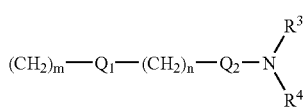

wherein $R^3$ and $R^4$ simultaneously or independently from each other may be hydrogen, $C_1$-$C_4$alkyl, aryl or together with N have the meaning of an optionally substituted heterocycle or heteroaryl;

m and n represent an integer from 0 to 3;

$Q_1$ and $Q_2$ represent, independently from each other, oxygen, sulfur or groups:

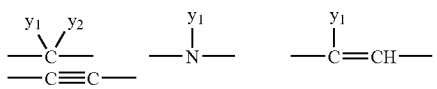

wherein the substituents $y_1$ and $y_2$ independently from each other may be hydrogen, halogen, an optionally substituted $C_1$-$C_4$ alkyl or aryl, hydroxy, $C_1$-$C_4$ alkoxy, $C_1$-$C_4$ alkanoyl, thiol, $C_1$-$C_4$ alkylthio, sulfonyl, $C_1$-$C_4$ alkylsulfonyl, sulfinyl, $C_1$-$C_4$ alkylsulfinyl, cyano, nitro or together form carbonyl or imino group;

$R^2$ may be hydrogen, carboxy or alkyloxycarbonyl;

as well as to pharmacologically acceptable salts and solvates thereof.

The term "halo", "hal" or "halogen" relates to a halogen atom which may be fluorine, chlorine, bromine or iodine.

The term "alkyl" relates to alkyl groups with the meaning of alkanes wherefrom radicals are derived, which radicals may be straight, branched or cyclic or a combination of straight and cyclic ones and branched and cyclic ones. The preferred straight or branched alkyls are e.g. methyl, ethyl, propyl, isopropyl, butyl, sec-butyl and tert-butyl. The preferred cyclic alkyls are e.g. cyclopentyl or cyclohexyl.

The term "haloalkyl" relates to alkyl groups which must be substituted with at least one halogen atom. The most frequent haloalkyls are e.g. chloromethyl, dichloromethyl, trifluoromethyl or 1,2-dichloropropyl.

The term "alkenyl" relates to alkenyl groups having the meaning of hydrocarbon radicals, which may be straight, branched or cyclic or are a combination of straight and cyclic ones or branched and cyclic ones, but having at least one carbon-carbon double bond. The most frequent alkenyls are ethenyl, propenyl, butenyl or cyclohexenyl.

The term "alkinyl" relates to alkinyl groups having the meaning of hydrocarbon radicals, which are straight or branched and contain at least one and at most two carbon-carbon triple bonds. The most frequent alkinyls are e.g. ethinyl, propinyl or butinyl.

The term "alkoxy" relates to straight or branched chains of alkoxy group. Examples of such groups are methoxy, propoxy, prop-2-oxy, butoxy, but-2-oxy or methylprop-2-oxy.

The term "aryl" relates to groups having the meaning of an aromatic ring, e.g. phenyl, as well as to fused aromatic rings. Aryl contains one ring with at least 6 carbon atoms or two rings with totally 10 carbon atoms and with alternating double (resonant) bonds between carbon atoms. The most frequently used aryls are e.g. phenyl or naphthyl. In general, aryl groups may be linked to the rest of the molecule by any available carbon atom via a direct bond or via a $C_1$-$C_4$ alkylene group such as methylene or ethylene.

The term "heteroaryl" relates to groups having the meaning of aromatic and partially aromatic groups of a monocyclic or bicyclic ring with 4 to 12 carbon atoms, at least one of them being a hetero atom such as O, S or N, and the available nitrogen atom or carbon atom is the binding site of the group to the rest of the molecule either via a direct bond or via a $C_1$-$C_4$ alkylene group defined earlier. Examples of this type are thiophenyl, pyrrolyl, imidazolyl, pyridinyl, oxazolyl, thiazolyl, pyrazolyl, tetrazolyl, pirimidinyl, pyrazinyl, quinolinyl or triazinyl.

The term "heterocycle" relates to five-member or six-member, fully saturated or partly unsaturated heterocyclic groups containing at least one hetero atom such as O, S or N, and the available nitrogen atom or carbon atom is the binding site of the group to the rest of the molecule either via a direct bond or via a $C_1$-$C_4$ alkylene group defined earlier. The most frequent examples are morpholinyl, piperidinyl, piperazinyl, pyrrolidinyl, pirazinyl or imidazolyl.

The term "alkanoyl" group relates to straight chains of acyl group such as formyl, acetyl or propanoyl.

The term "aroyl" group relates to aromatic acyl groups such as benzoyl.

The term "optionally substituted alkyl" relates to alkyl groups which may be optionally additionally substituted with one, two, three or more substituents. Such substituents may be halogen atom (preferably fluorine or chlorine), hydroxy, $C_1$-$C_4$ alkoxy (preferably metboxy or ethoxy), thiol, $C_1$-$C_4$ alkylthio (preferably methylthio or ethylthio), amino, N—($C_1$-$C_4$) alkylamino (preferably N-methylamino or N-ethylamino), N,N-di($C_1$-$C_4$-alkyl)-amino (preferably dimethylamino or diethylamino), sulfonyl, $C_1$-$C_4$ alkylsulfonyl (preferably methylsulfonyl or ethylsulfonyl), sulfinyl, $C_1$-$C_4$ alkylsulfinyl (preferably methylsulfinyl).

The term "optionally substituted alkenyl" relates to alkenyl groups optionally additionally substituted with one, two or three halogen atoms. Such substituents may be e.g. 2-chloroethenyl, 1,2-dichloroethenyl or 2-bromo-propene-1-yl.

The term "optionally substituted aryl, heteroaryl or heterocycle" relates to aryl, heteroaryl or heterocyclic groups which may be optionally additionally substituted with one or two substituents. The substituents may be halogen (preferably chlorine or fluorine), $C_1$-$C_4$ alkyl (preferably methyl, ethyl or isopropyl), cyano, nitro, hydroxy, $C_1$-$C_4$ alkoxy (preferably methoxy or ethoxy), thiol, $C_1$-$C_4$ alkylthio (preferably methylthio or ethylthio), amino, N—($C_1$-$C_4$) alkylamino (preferably N-methylamino or N-ethylamino), N,N-di($C_1$-$C_4$-alkyl)-amino (preferably N,N-dimethylamino or N,N-diethylamino), sulfonyl, $C_1$-$C_4$ alkylsulfonyl (preferably methylsulfonyl or ethylsulfonyl), sulfinyl, $C_1$-$C_4$ alkylsulfinyl (preferably methylsulfinyl).

When X has the meaning of $NR^a$ and $R^a$ has the meaning of a protecting group, then $R^a$ relates to groups such as alkyl (preferably methyl or ethyl), alkanoyl (preferably acetyl), alkoxycarbonyl (preferably methoxycarbonyl or tert-butoxycarbonyl), arylmethoxycarbonyl (preferably benzyloxycarbonyl), aroyl (preferably benzoyl), arylalkyl (preferably benzyl), alkylsilyl (preferably trimethylsilyl) or alkylsilylalkoxyalkyl (preferably trimethylsilylethoxymethyl).

When $R^3$ and $R^4$ together with N have the meaning of heteroaryl or heterocycle, this means that such heteroaryls or heterocycles have at least one carbon atom replaced by a nitrogen atom through which the groups are linked to the rest of the molecule. Examples of such groups are morpholine-4-yl, piperidine-1-yl, pyrrolidine-1-yl, imidazole-1-yl or piperazine-1-yl.

The term "pharmaceutically suitable salts" relates to salts of the compounds of the formula I and include e.g. salts with $C_1$-$C_4$ alkylhalides (preferably methyl bromide, methyl chloride) (quaternary ammonium salts), with inorganic acids (hydrochloric, hydrobromic, phosphoric, metaphosphoric, nitric or sulfuric acids) or with organic acids (tartaric, acetic, citric, maleic, lactic, fumaric, benzoic, succinic, methane sulfonic or p-toluene sulfonic acids).

Some compounds of the formula I may form salts with organic or inorganic acids or bases and these are also included in the present invention.

Solvates (most frequently hydrates) which may form compounds of the formula I or salts thereof are also an object of the present invention.

Depending upon the nature of particular substituents, the compounds of the formula I may have geometric isomers and one or more chiral centres so that there can exist enantiomers or diastereoisomers. The present invention also relates to such isomers and mixtures thereof, including racemates.

The present invention also relates to all possible tautomeric forms of particular compounds of the formula I.

A further object of the present invention relates to the preparation of compounds of the formula I according to processes comprising:

a) for compounds of the formula I, wherein $R^1$ and $R^2$ represent, independently from each other, carboxyl group, $C_1$-$C_6$ alkyloxycarbonyl, aryloxycarbonyl or arylalkyloxycarbonyl, a cyclisation of α-diketones of the formula III:

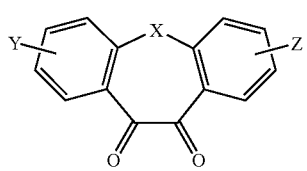

III with compounds of the formula IV:

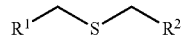

IV b) for compounds of the formula I, wherein $Q_1$ has a meaning of —O—, a reaction of alcohols of the formula V:

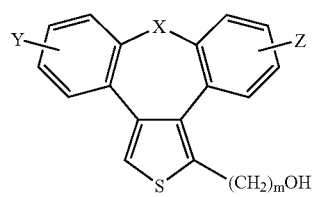

V with compounds of formula VI:

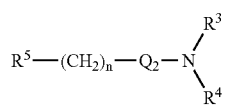

VI wherein $R^5$ has the meaning of a leaving group;

c) for the compounds of the formula I, wherein $Q_1$ has a meaning of —O—, —NH—, —S— or —C≡C—, a reaction of the compounds of the formula Va:

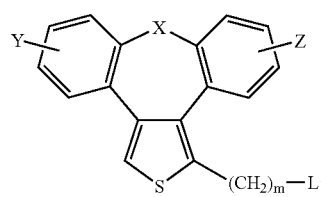

Va wherein $L^1$ has the meaning of a leaving group, with compounds of the formula VIa:

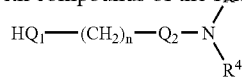

VIa d) for the compounds of the formula I, wherein $Q_1$ has a meaning of —O—, —NH— or —S—, a reaction of the compounds of the formula Vb:

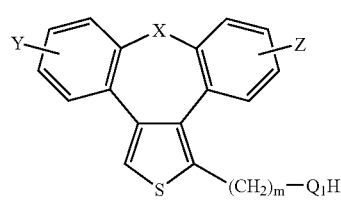

Vb with the compounds of the formula VI, wherein $R^5$ has the meaning of a leaving group;

e) for the compounds of the formula I, wherein $Q_1$ has the meaning of —C≡C—,
a reaction of the compounds of the formula Vb, wherein $Q_1$ has the meaning of carbonyl, with phosphorous ylides.

Preparation Methods:

a) Cyclization of α-diketones of the formula III and of compounds of the formula IV, wherein $R^1$ and $R^2$ simultaneously or independently from each other represent $C_1$-$C_6$-alkyloxycarbonyl, aryloxycarbonyl or arylalkyloxycarbonyl, is carried out by methods disclosed for the preparation of analogous compounds (Chadwick D J et al., *J. Chem. Soc. Perkin Trans. I*, 1972, 2079-81). The reaction of cyclization is carried out in alcohols (most frequently in tert-butanol) in the presence of alcoholates (preferably potassium tert-butylate).

The starting compounds for this reaction are already known or they are prepared by methods described for the preparation of analogous compounds: for α-diketones of formula III in e.g. Leonard N. J. et al., *J. Am. Chem. Soc.*, 1955, 77:5078, U.S. Pat. No. 3,711,489 or Lombardino J. G, *J. Heterocyclic Chem.*, 1974, 11:17-21; or for thioethers of formula IV e.g. in Overberger C. G. et al., *J. Am. Chem. Soc.*, 1950, 72:4958-61. The so obtained compounds may be purified, isolated and characterized or may be subjected to further transformation without isolation.

b) The compounds of the formula I according to the present process may be prepared by reaction of alcohols of the formula V and compounds of the formula VI, wherein $R^5$ has the meaning of a leaving group, which may be a halogen atom (most frequently bromine, iodine or chlorine) or sulfonyloxy group (most frequently trifluoromethylsulfonyloxy or p-toluenesulfonyloxy). The condensation reaction may be carried out according to methods disclosed for the preparation of analogous compounds (Menozzi G et al., *J. Heterocyclic Chem.*, 1997, 34:963-968 or WO 01/87890). The reaction is carried out at a temperature from 20° C. to 100° C. during 1 to 24 hours in a two-phase system (preferably with 50% NaOH/toluene) in the presence of a phase transfer catalyst (preferably benzyl triethyl ammonium chloride, benzyl triethyl ammonium bromide, cetyl trimethyl bromide). After the treatment of the reaction mixture, the products formed are isolated by recrystallization or chromatography on a silica gel column.

The starting compounds for the preparation of alcohols of the formula V are compounds of the formula I, wherein $R^1$ and $R^2$ independently from each other have the meaning of carboxyl or ester group (ethyloxycarbonyl, methyloxycarbonyl), which by decarboxylation give compounds of the formula I, wherein $R^2$ has the meaning of hydrogen and $R^1$ has the meaning of an ester group, which by reduction yield alcohols of the formula V. Decarboxylation is carried out by pyrolysis at 250-300° C. in the presence of metals, preferably copper. The reduction reaction is carried out by the use of metal hydrides such as lithium aluminum hydride or sodium borohydride. Further, the alcohols of the formula V may be prepared by hydrolysis of the corresponding esters (in alkaline or acidic mediums).

The starting compounds of the formula VI are already known or are prepared according to methods disclosed for the preparation of analogous compounds.

c) Compounds of the formula I may be prepared according to the present process by reacting compounds of the formula Va, wherein $L^1$ has the meaning of a leaving group defined earlier for $R^5$, and compounds of the formula VIa, wherein $Q_1$ has the meaning of oxygen, nitrogen, sulfur or —C≡C—. The most suitable condensation reactions are reactions of nucleophilic substitution on a saturated carbon atom as disclosed in the literature.

The starting compounds of the formula Va (most frequently halides) may be obtained by halogenation (e.g. bromination or chlorination) of alcohols of the formula V with the usual halogenating agents (e.g. hydrobromic acid, $PBr_3$, $SOCl_2$ or $PCl_5$) by processes as disclosed in the literature. The obtained compounds may be isolated or may be used without isolation as suitable intermediates for the preparation of the compounds of the formula I.

The starting compounds of the formula VIa are already known or are prepared according to methods disclosed for the preparation of analogous compounds.

d) The compounds of the formula I, wherein $Q_1$ has the meaning of a hetero atom —O—, —NH— or —S—, may be prepared by the condensation of the compounds of the formula Vb and of compounds of the formula VI, wherein $R^5$ has the meaning of a leaving group as defined earlier. The reaction may be carried out at reaction conditions disclosed in the method b) or at conditions of the nucleophilic substitution reactions disclosed in the literature. The starting alcohols, amines and thiols may be obtained by a reaction of water, ammonia or hydrogen sulfide with compounds Va according to processes disclosed in the literature.

e) The alcohols of the structure V may be oxidized to corresponding compounds of the formula Vb, wherein $Q_1$ has the meaning of carbonyl, which may further, by reaction with corresponding ylide reagents, result in a prolongation of the chain and in the formation of an alkenyl substituent with carbonyl or ester groups as disclosed in HR patent application No.20000310.

Besides the above-mentioned reactions, the compounds of the formula I may be prepared by transforming other compounds of the formula I and it is to be understood that the present invention also comprises such compounds and processes. A special example of a change of a functional group is the reaction of the aldehyde group with chosen phosphorous ylides resulting in a prolongation of the chain and the formation of an alkenyl substituent with carbonyl or ester groups as disclosed in HR patent application No. 20000310. These reactions are carried out in solvents such as benzene, toluene or hexane at elevated temperature (most frequently at boiling temperature).

By reacting the compounds of the formula Va with 1-alkyne in an alkaline medium (such as sodium amide in ammonia), compounds of the formula I, wherein $Q_1$ is —C≡C—, are obtained. The reaction conditions of this process are disclosed in the literature. At similar reaction conditions (nucleophilic substitution) various ether, thioether or amine derivatives may be prepared.

The formylation of the compounds of the formula I by processes such as e.g. Vilsmeier acylation or reaction of n-BuLi and dimethylformamide is a further general example of a transformation. The reaction conditions of these processes are well-known in the literature.

By hydrolysis of the compounds of the formula I having nitrile, amide or ester groups, there may be prepared compounds with a carboxyl group, which are suitable intermediates for the preparation of other compounds with novel functional groups such as e.g. esters, amides, halides, anhydrides, alcohols or amines.

Oxidation or reduction reactions are a further possibility of the change of substituents in the compounds of the formula I. The most frequently used oxidation agents are peroxides (hydrogen peroxide, m-chloroperbenzoic acid or benzoyl peroxide) or permanganate, chromate or perchlorate ions. Thus e.g. by the oxidation of an alcohol group by pyridinyl dichromate or pyridinyl chlorochromate, an aldehyde group is formed, which group may be converted to a carboxyl group by further oxidation. By oxidation of the compounds of the formula I, wherein $R^1$ has the meaning of alkyl, with lead tetraacetate in acetic acid or with N-bromosuccinimide using a catalytic amount of benzoyl peroxide, a corresponding carbonyl derivative is obtained.

By a selective oxidation of alkylthio group, alkylsulfinyl or alkylsulfonyl groups may be prepared.

By the reduction of the compounds with a nitro group, the preparation of amino compounds is made possible. The reaction is carried out under usual conditions of catalytic hydrogenation or electrochemically. By catalytic hydrogenation using palladium on carbon, alkenyl substituents may be converted to alkyl ones or the nitrite group can be converted to aminoalkyl.

Various substituents of the aromatic structure in the compounds of the formula I may be introduced by standard substitution reactions or by usual changes of individual functional groups. Examples of such reactions are aromatic substitutions, alkylations, halogenation, hydroxylation as well as oxidation or reduction of substituents. Reagents and reaction conditions are known from the literature. Thus e.g. by aromatic substitution a nitro group is introduced in the presence of concentrated nitric acid and sulfuric acid. By using acyl halides or alkyl halides, the introduction of an acyl group or an alkyl group is made possible. The reaction is carried out in the presence of Lewis acids such as aluminum- or iron-trichloride in conditions of Friedel-Crafts reaction. By the reduction of the nitro group, an amino group is obtained, which is by a diazotizing reaction converted to a suitable starting group, which may be replaced with one of the following groups: H, CN, OH, Hal.

In order to prevent undesired interaction in chemical reactions, it is often necessary to protect certain groups such as e.g. hydroxy, amino, thio or carboxy. For this purpose a great number of protecting groups may be used [Green T W, Wuts P G H, Protective Groups in Organic Synthesis, John Wiley and Sons, 1999] and the choice, use and elimination thereof are conventional methods in chemical synthesis.

A convenient protection for amino or alkylamino groups are groups such as e.g. alkanoyl (acetyl), alkoxycarbonyl (methoxycarbonyl, ethoxycarbonyl or tert-butoxycarbonyl); arylmethoxycarbonyl (benzyloxycarbonyl), aroyl (benzoyl) or alkylsilyl (trimethylsilyl or trimethylsilylethoxymethyl) groups. The conditions of removing a protecting group depend upon the choice and the characteristics of this group. Thus e.g. acyl groups such as alkanoyl, alkoxycarbonyl or aroyl may be eliminated by hydrolysis in the presence of a base (sodium hydroxide or potassium hydroxide), tert-butoxycarbonyl or alkylsilyl (trimethylsilyl) may be eliminated by treatment with a suitable acid (hydrochloric, sulfuric, phosphoric or trifluoroacetic acid), whereas arylmethoxycarbonyl group (benzyloxycarbonyl) may be eliminated by hydrogenation using a catalyst such as palladium on carbon.

Salts of the compounds of the formula I may be prepared by generally known processes such as e.g. by reacting the compounds of the formula I with a corresponding base or acid in an appropriate solvent or solvent mixture e.g. ethers (diethylether) or alcohols (ethanol, propanol or isopropanol).

Another object of the present invention concerns the use of the present compounds in the therapy of inflammatory diseases and conditions, especially of all diseases and conditions induced by excessive TNF-α and IL-1 secretion.

The inhibitors of production of cytokins or inflammation mediators, which are the object of the present invention, or pharmacologically acceptable salts thereof may be used in the production of drugs for the treatment and prophylaxis of any pathological condition or disease induced by excessive unregulated production of cytokins or inflammation mediators, which drugs should contain an effective dose of said inhibitors.

The present invention specifically relates to an effective dose of TNF-α inhibitor, which may be determined by usual methods.

Further, the present invention relates to a pharmaceutical formulation containing an effective non-toxic dosis of the present compounds as well as pharmaceutically acceptable carriers or solvents.

The preparation of pharmaceutical formulations may include blending, granulating, tabletting and dissolving ingredients. Chemical carriers may be solid or liquid. Solid carriers may be lactose, sucrose, talcum, gelatine, agar, pectin, magnesium stearate, fatty acids etc. Liquid carriers may be syrups, oils such as olive oil, sunflower oil or soya bean oil, water etc. Similarly, the carrier may also contain a component for a sustained release of the active component such as e.g. glyceryl monostearate or glyceryl distearate. Various forms of pharmaceutical formulations may be used. Thus, if a solid carrier is used, these forms may be tablets, hard gelatine capsules, powder or granules that may be administered in capsules per os. The amount of the solid carrier may vary, but it is mainly from 25 mg to 1 g. If a liquid carrier is used, the formulation would be in the form of a syrup, emulsion, soft gelatine capsules, sterile injectable liquids such as ampoules or non-aqueous liquid suspensions.

Compounds according to the present invention may be applied perorally, parenterally, locally, intranasally, intrarectally and intravaginally. The parenteral route herein means intravenous, intramuscular and subcutaneous applications. Appropriate formulations of the present compounds may be used in the prophylaxis as well as in the treatment of various diseases and pathological inflammatory conditions induced by an excessive unregulated production of cytokins or inflammation mediators, primarily TNF-α. They comprise rheumatoid arthritis, rheumatoid spondylitis, osteoarthritis and other arthritic pathological conditions and diseases, eczemas, psoriasis and other inflammatory skin conditions such as burns induced by UV radiation (sun rays and similar UV sources), inflammatory eye diseases, Crohn's disease, ulcerative colitis and asthma.

The inhibitory action of the present compounds upon TNF-α and IL-1 secretion was determined by the following in vitro and in vivo experiments:

Determination of TNF-α and IL-1 Secretion in Human Peripheral Blood Mononuclear Cells in vitro Human peripheral blood mononuclear cells (PBMC) were prepared from heparinized whole blood after separating PBMC on Ficoll-Paque™Plus (Amersham-Pharmacia). To determine the TNF-α level, $3.5-5 \times 10^4$ cells were cultivated in a total volume of 200 µl for 18 to 24 hours on microtitre plates with a flat bottom (96 wells, Falcon) in RPMI 1640 medium, into which there were added 10% FBS (Fetal Bovine Serum, Biowhittaker) previously inactivated at 54° C./30 min, 100 units/ml of penicillin, 100 mg/ml of streptomycin and 20 mM HEPES (GIBCO). The cells were incubated at 37° C. in an atmosphere with 5% $CO_2$ and 90% humidity. In a negative control the cells were cultivated only in the medium (NC), whereas in a positive control TNF-α secretion was triggered by adding 1 ng/ml of lipopolysaccharides (LPS, E. coli serotype 0111:B4, SIGMA) (PC). The effect of the tested substances upon TNF-α secretion was investigated after adding them into cultures of cells stimulated by LPS (TS). The TNF-α level in the cell supernatant was determined by ELISA procedure according to the suggestions of the producer (R&D Systems). The test sensitivity was <3 pg/ml TNF-α. The IL-1 level was determined in an assay under the same conditions and with the same number of cells and the same concentration of stimuli stimulus by ELISA procedure (R&D Systems). The percentage of inhibition of TNF-α or IL-1 production was calculated by the equation:

% inhibition=$[1-(TS-NC)/(PC-NC)]*100$.

The $IC_{50}$ value was defined as the substance concentration, at which 50% of TNF-α production were inhibited.

Compounds showing $IC_{50}$ with 20 μM or lower concentrations are active.

Determination of TNF-α and IL-1 Secretion in Mouse Peritoneal Macrophages in vitro In order to obtain peritoneal macrophages, Balb/C mouse strain males, age 8 to 12 weeks, were injected i.p. with 300 μg of zymosan (SIGMA) dissolved in a phosphate buffer (PBS) in a total volume of 0.1 ml/mouse. After 24 hours the mice were euthanized according to the Laboratory Animal Welfare Act. The peritoneal cavity was washed with a sterile physiological solution (5 ml). The obtained peritoneal macrophages were washed twice with a sterile physiological solution and, after the last centrifugation (350 g/10 min), resuspended in RPMI 1640, into which 10% of FBS portion were added. In order to determine TNF-α secretion, $5 \times 10^4$ cells/well were cultivated in a total volume of 200 μl for 18 to 24 hours on microtitre plates with a flat bottom (96 wells, Falcon) in RPMI 1640 medium, into which 10% FBS (Fetal Bovine Serum, Biowhittaker) inactivated by heat, 100 units/ml of penicillin, 100 mg/ml of streptomycin, 20 mM HEPES and 50 μM 2-mercaptoethanol (all of GIBCO) were added. The cells were incubated at 37° C. in an atmosphere with 5% $CO_2$ and 90% humidity. In a negative control the cells were cultivated only in a medium (NC), whereas in a positive control the TNF-α secretion was triggered by adding 10 ng/ml of lipopolysaccharides (LPS, *E. coli* serotype 0111:B4, SIGMA) (PC). The effect of the substances upon the TNF-α secretion was investigated after adding them into cultures of cells stimulated with LPS (TS). The TNF-α level in the cell supernatant was determined by ELISA procedure (R&D Systems, Biosource). The IL-1 level was determined in an assay identical to the assay for TNF-α by ELISA procedure (R&D Systems). The percentage of inhibition of TNF-α or IL-1 production was calculated by the equation:

% inhibition=$[1-(TS-NC)/(PC-NC)]*100$.

The $IC_{50}$ value was defined as the substance concentration, at which 50% of TNF-α production were inhibited.

Compounds showing $IC_{50}$ with 10 μM or lower concentrations are active.

In vivo Model of LPS-Induced Excessive TNF-α or IL-1 Secretion in Mice

TNF-α or IL-1 secretion in mice was induced according to the already disclosed method (Badger AM et al., *J. Pharmac. Env. Therap.*, 1996, 279:1453-1461). Balb/C males, age 8 to 12 weeks, in groups of 6 to 10 animals were used. The animals were treated p.o. either with a solvent only (in negative and in positive controls) or with solutions of substances 30 minutes prior to i.p. treatment with LPS (*E. coli* serotype 0111:B4, Sigma) in a dose of 25 μg/animal. Two hours later the animals were euthanized by means of i.p. Roumpun (Bayer) and Ketanest (Parke-Davis) injection. A blood sample of each animal was taken into a Vacutainer tube (Becton Dickinson) and the plasma was separated according to the producer's instructions. The TNF-α level in the plasma was determined by ELISA procedure (Biosource, R&D Systems) according to the producer's instructions. The test sensitivity was <3 pg/ml TNF-α. The IL-1 level was determined by ELISA procedure (R&D Systems). The percentage of inhibition of TNF-α or IL-1 production Was calculated by the equation:

% inhibition=$[1-(TS-NC)/(PC-NC)]*100$.

Active are the compounds showing 30% or more inhibition of TNF-α production at a dosis of 10 mg/kg.

Writhing Assay for Analgetic Activity

In this assay pain is induced by the injection of an irritant, most frequently acetic acid, into the peritoneal cavity of mice. Animals react with characteristic writhings, which has given the name of the assay (Collier H O J et al., *Pharmac. Chemother.*, 1968, 32:295-310; Fukawa K et al., *J. Pharmacol. Meth.*, 1980, 4:251-259; Schweizer A et al., *Agents Actions*, 1988, 23:29-31). The assay is convenient for the determination of analgetic activity of compounds. Procedure: male Balb/C mice (Charles River, Italy), age 8 to 12 weeks, were used. A control group received methyl cellulose p.o. 30 minutes prior to i.p. application of acetic acid in a concentration of 0.6%, whereas test groups received standard (acetylsalicylic acid) or test substances in methyl cellulose p.o. 30 minutes prior to i.p. application of 0.6% acetic acid (volume 0.1 ml/10 g). The mice were placed individually under glass funnels and the number of writhings was registered for 20 minutes for each animal. The percentage of writhing inhibition was calculated according to the equation:

% inhibition=(mean value of number of writhings in the control group−number of writhings in the test group)/number of writhings in the control group*100.

Active are the compounds showing such analgetic activity as acetylsalicylic acid or better.

In vivo Model of LPS-Induced Shock in Mice

Male Balb/C mice (Charles River, Italy), age 8 to 12 weks, were used. LPS isolated from *Serratie marcessans* (Sigma, L-6136) was diluted in sterile physiological solution. The first LPS injection was administered intradermally in a dosis of 4 μg/mouse. 18 to 24 hours later, LPS was administered i.v. in a dosis of 200 μg/mouse. A control group received two LPS injections as disclosed above. The test groups received substances p.o. half an hour prior to each LPS application. Survival after 24 hours was observed.

Active are the substances at which the survival at a dosis of 30 mg/kg was 40% or more.

Compounds from Example 14 show activity in at least two investigated assays though these results only represent an illustration of the biological activity of the compounds and should not limit the invention in any way.

PREPARATION METHODS WITH EXAMPLES

The present invention is illustrated by the following Examples which are in no way a limitation thereof.

Example 1

8-Oxa-2-thia-dibenzo[e,h]azulene-1,3-udicarboxylic acid monoethyl ester (1)

A solution of dibenzo[b,f]oxepin-10,11-dione (III; X=O, Y=Z=H) (0.004 mole) and thioether (IV; $R^1$, $R^2$=Et) (0.008 mole) in tert-butanol was added to a potassium butoxide solution (0.013 mole) in 5 ml of tert-butanol (10 ml), heated to 60° C. After 30 minutes of stirring at 60° C., the reaction mixture was cooled and acidified with 5 M aqueous HCl solution (10 ml), whereupon the majority of the solvent was evaporated at the temperature of 30° C. and the pressure of 30 hPa. Diethyl ether (20 ml) was added to the residue and then the solution was extracted with 2 M $NH_4OH$ solution (10 ml). The combined extracts were acidified with diluted HCl to an acidic reaction and dicarboxylate in the form of brown crystals was obtained.

Example 2

5-Chloro-8-oxa-2-thia-dibenzo[e,h]azulene-1,3-dicarboxylic acid 1-methyl ester (2)

5-Chloro-8-oxa-2-thia-dibenzo[e,h]azulene-1,3-dicarboxylic acid 3-methyl ester (3)

According to the process of Example 1, starting from 2-chloro-dibenzo[b,f]oxepin-10,11-dione (III; X=O, Y=2-Cl, Z=H) and thioether (IV; $R^1$, $R^2$=Me), a mixture of dicarboxylates in the form of a brown oil was obtained.

Example 3

2,8-Dithia-dibenzo[e,h]azulene-1,3-dicarboxylic acid monoethyl ester (4)

According to the process of Example 1, starting from dibenzo[b,f]tiepin-10,11-dione (III; X=S, Y=Z=H) and thioether (IV; $R^5$=Et), dicarboxylate in the form of brown crystals was obtained.

Example 4

8-Oxa-2-thia-dibenzo[e,h]azulene-1-carboxylic acid ethyl ester (5)

8-Oxa-2-thia-dibenzo[e,h]azulene (9)

A homogenous mixture of dicarboxylate 1 (200 mg) and copper (150 mg) was heated for 2 hours at 300° C. After the cooling of the reaction mixture, diethyl ether was added thereto and the undissolved copper oxide was filtered off. The filtrate was evaporated under reduced pressure and the obtained product mixture was separated by chromatography on a column. Compounds 5 and 9 in crystal form were isolated.

Example 5

5-Chloro-8-oxa-2-thia-dibenzo[e,h]azulene-1-carboxylic acid methyl ester (6)

11-Chloro-8-oxa-2-thia-dibenzo[e,h]azulene-1-carboxylic acid methyl ester (7)

5-Chloro-8-oxa-2-thia-dibenzo[e,h]azulene (10)

According to the process of Example 4, starting from a mixture of dicarboxylates 2 and 3, a mixture of two mono carboxylates, 6 and 7, and of the compound 10 was obtained. The compound 10 was separated from the monocarboxylate mixture by chromatography on a column. Carboxylates 6 and 7 were separated and determined by GC-MS as two close peaks with m/z=314 ($MH^+$).

Example 6

2,8-Dithia-dibenzo[e,h]azulene-1-carboxylic acid ethyl ester (8)

2,8-Dithia-dibenzo[e,h]azulene (11)

According to the process of Example 4, starting from dicarboxylate 4 there were prepared compounds 8 and 11. The mixture of the compounds was separated by chromatography on a column to give both products in crystal form.

Example 7

(8-Oxa-2-thia-dibenzo[e,h]azulene-1-yl)-methanol (12)

To a suspension of $LiAlH_4$ in dry ether (10 mmoles in 15 ml of dry ether) an ether solution of the ester 5 (2 mmoles in 15 ml of dry ether) was added drop by drop. The reaction mixture was stirred at room temperature for 4 hours. After the complete quantity of the ester had been reacted (the course of the reaction was followed by thin layer chromatography), the excess of $LiAlH_4$ was decomposed by the addition of diethyl ether and water. The obtained white precipitate was filtered off and after drying on anhydrous $Na_2SO_4$ the filtrate was evaporated under reduced pressure. The crude product was purified by chromatography on a column to give a pure product in the form of yellowish crystals.

Example 8

(5-Chloro-8-oxa-2-thia-dibenzo[e,h]azulene-1-yl)-methanol (13)

(11-Chloro-8-oxa-2-thia-dibenzo[e,h]azulene-1-yl)-methanol (14)

According to the process of Example 8, starting from the mixture of esters 6 and 7 there was prepared a mixture of the title alcohols, which were separated by column chromatography to give pure substances in the form of yellowish crystals.

Example 9

(2,8-Dithia-dibenzo[e,h]azulene-1-yl)-methanol (15)

According to the process of Example 8, starting from the corresponding ester 8 there was prepared an alcohol in the form of brown crystals.

TABLE 1

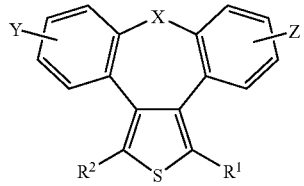

| Comp. | X | Y | Z | R² | R¹ | ¹H NMR (ppm) |
|---|---|---|---|---|---|---|
| 1 | O | H | H | CO₂H | CO₂Et | 1.33 (t, 3H); 4.32 (m, 2H); 7.14-7.19 (m, 2H); 7.31-7.42 (m, 7.54-7.64 (m, 2H) (CDCl₃) |
| 2 | O | 5-Cl | H | CO₂H | CO₂Me | |
| 3 | O | H | 11-Cl | CO₂H | CO₂Me | |
| 4 | S | H | H | CO₂H | CO₂Et | 1.15 (t, 3H); 4.22 (m, 2H); 7.29-7.40 (m, 4H); 7.54-7.58 (m, 7.63-7.66 (m, 2H); 13.5 (bs, 1H) (DMSO-d₆) |
| 5 | O | H | H | H | CO₂Et | 1.32 (t, 3H); 4.33 (m, 2H); 7.17-7.67 (m, 9H) (CDCl₃) |
| 6 | O | 5-Cl | H | H | CO₂Me | |
| 7 | O | H | 11-Cl | H | CO₂Me | |
| 8 | S | H | H | H | CO₂Et | 1.25 (t, 3H); 4.26 (m, 2H); 7.24-7.35 (m, 4H); 7.50-7.54 (m, 2H); 7.58 (s, 1H); 7.62-7.67 (m, 2H) (CDCl₃) |
| 9 | O | H | H | H | H | 7.24-7.30 (m, 2H); 7.37-7.41 (m, 4H); 7.66-7.69 (m, 2H); 7.97 (s, 2H) (DMSO-d₆) |
| 10 | O | 5-Cl | H | H | H | 7.19-7.58 (m, 9H) (CDCl₃) |
| 11 | S | H | H | H | H | 7.25-7.37 (m, 4H); 7.49 (s, 2H); 7.53-7.57 (m, 2H); 7.64-7.68 (m, 2H) (CDCl₃) |
| 12 | O | H | H | H | CH₂OH | 1.76 (bs, 1H); 4.97 (bd, 2H); 7.17-7.38 (m, 6H); 7.46 (s, 1H); 7.54-7.60 (m, 2H) (CDCl₃) |
| 13 | O | 5-Cl | H | H | CH₂OH | 4.88 (bs, 1H); 4.93 (s, 2H); 7.27-7.43 (m, 5H); 7.67-7.70 (m, 2H); 7.80 (s, 1H) (CD₃COCD₃) |
| 14 | O | H | 11-Cl | H | CH₂OH | 4.93 (bs, 3H); 7.23-7.29 (m, 1H); 7.36-7.46 (m, 4H); 7.65-7.68 (m, 1H); 7.73 (s, 1H); 7.82 (d, 1H) (CD₃COCD₃) |
| 15 | S | H | H | H | CH₂OH | 1.84 (bs, 1H); 4.13 (m, 2H); 7.23-7.38 (m, 4H); 7.40 (s, 1H), 7.48-7.50 (m, 2H); 7.62-7.72 (m, 2H) (CDCl₃) |

Example 10 a) Dimethyl-[3-(8-oxa-2-thia-dibenzo[e,h]azulene-1-ylmethoxy)-propyl]-amine To a 3-dimethylaminopropylchloride-hydrochloride solution (2.5 mmoles) in 50% sodium hydroxide (3 ml), benzyltriethylammonium chloride (0.3 mmole) and a toluene solution of the alcohol 12 (0.25 mmole) were added. The reaction mixture was heated under vigorous stirring and refluxing for 4 hours. Then it was cooled to room temperature, diluted with water and extracted with dichloromethane. After purification by column chromatography an oily product was isolated.

¹H NMR (ppm, CDCl₃): 2.08 (m, 2H); 2.58 (s, 6H); 2.84 (m, 2H); 3.69 (m, 2H); 4.75 (bd, 2H); 7.16-7.36 (m, 6H), 7.46 (s, 1H); 7.47-7.56 (m, 2H).

b) Dimethyl-[2-(8-oxa-2-thia-dibenzo[e,h]azulene-1-ylmethoxy)-ethyl]-amine

Starting from the alcohol 12 (0.25 mmole) and 2-dimethylaminoethylchloride-hydrochloride (2.5 mmoles), an oily product was obtained.

¹H NMR (ppm, CDCl₃): 2.52 (s, 6H); 2.86 (bs, 2H); 3.85 (bs, 2H); 4.80 (bd, 2H); 7.16-7.36 (m, 6H); 7.46 (s, 1H); 7.49-7.56 (m, 2H).

c) 3-(8-Oxa-2-thia-dibenzo[e,h]azulene-1-yl-methoxy)-propylamine

Starting from the alcohol 12 (0.25 mmole) and 3-chloropropylamine-hydrochloride (2.5 mmoles), an oily product was obtained.

¹H NMR (ppm, CDCl₃): 1.99 (m, 2H); 3.05 (t, 2H); 3.70 (bs, 2H); 4.3-4.5 (b, 2H); 4.72 (bs, 2H); 7.15-7.60 (m, 9H).

Example 11 a) 3-(5-Chloro-8-oxa-2-thia-dibenzo[e,h]azulene-1-ylmethoxy)-propylamine

To a solution of 3-chloropropylamine-hydrochloride (2.2 mmoles) in 50% sodium hydroxide (3 ml), benzyltriethylammonium chloride (0.3 mmole) and toluene solution of the alcohol 13 (0.22 mmole) were added. The reaction mixture was heated under vigorous stirring and refluxing for 5 hours. Then it was cooled to room temperature, diluted with water and extracted with dichloromethane. After purification by column chromatography an oily product was isolated.

MS (m/z): 372 (MH⁺).

b) [2-(5-Chloro-8-oxa-2-thia-dibenzo[e,h]azulene-1-ylmethoxy)-ethyl]-dimethyl-amine Starting from the alcohol 13 (0.29 mmole) and 2-dimethylaminoethylchloride-hydrochloride (2.9 mmoles), an oily product was obtained.

MS (m/z): 386 (NM⁺).

c) [3-(5-Chloro-8-oxa-2-thia-dibenzo[eh]azulene-1-ylmethoxy)-propyl]-dimethyl-amine Starting from the alcohol 13 (0.22 mmole) and 3-dimethylaminopropylchloride-hydrochloride (2.2 mmoles), an oily product was obtained.

MS (m/z): 400 (MH⁺);

Example 12 a) [2-(11-Chloro-8-oxa-2-thia-dibenzo[e,h]azulene-1-ylmethoxy)-ethyl]-dimethyl-amine To a solution of 2-dimethylaminoethylchloride-hydrochloride (1.8 mmoles) in 50% sodium hydroxide (3 ml), benzyltriethylammonium chloride (0.3 mmole) and toluene solution of the alcohol 14 (0.18 mmole) were added. The reaction mixture was heated under vigorous stirring and refluxing for 5 hours. Then it was cooled to room temperature, diluted with water and extracted by dichloromethane. After purifiaction by column chromatograpy an oily product was isolated.

MS (m/z): 386 (MH⁺).

b) 3-(11-Chloro-8-oxa-2-thia-dibenzo[e,h]azulene-1-ylmethoxy)-propylamine

Starting from the alcohol 14 (0.18 mmole) and 3-chloropropylamine-hydrochloride (1.8 mmoles), an oily product was obtained.

$^1$H NMR (ppm, CD$_3$COCD$_3$): 1.82 (s, 2H); 1.97 (t, 2H); 3.36 (t, 2H); 3.76 (bs, 2H); 4.74 (s, 2H); 7.26-7.82 (m, 8H); MS (m/z): 372 (MH⁺).

Example 13 a) [3-(2,8-Dithia-dibenzo[e,h]azulene-1-ylmethoxy)-propyl]-dimethyl-amine

To a solution of 3-dimethylaminopropylchloride-hydrochloride (6.7 mmoles) in 50% sodium hydroxide (5 ml), benzyltriethylammonium chloride (0.88 mmole) and toluene solution of the alcohol 15 (0.67 mmole) were added. The reaction mixture was heated under vigorous stirring and refluxing for 5 hours. Then it was cooled to room temperature, diluted with water and extracted by dichloromethane. After purification by column chromatograpy an oily product was isolated.

$^1$H NMR (ppm, CDCl$_3$): 2.04 (p, 2H); 2.57 (s, 6H); 2.82 (bs, 2H); 3.61 (m, 2H); 4.67 (m, 2H); 7.27-7.71 (m, 8H); 7.40 (s, 1H).

b) [2-(2,8-Dithia-dibenzo[e,h]azulene-1-ylmethoxy)-ethyl]-dimethyl-amine

Starting from the alcohol 15 (0.67 mmole) and 2-dimethylaminoethylchloride-hydrochloride (6.7 mmoles), an oily product was obtained;

$^1$H NMR (ppm, CDCl$_3$): 2.49 (s, 6H); 2.86 (bs, 2H); 3.78 (m, 2H); 4.72 (m, 2H); 7.23-7.70 (m, 8H); 7.40 (s, 1H).

c) 3-(2,8-Dithia-dibenzo[e,h]azulene-1-ylmethoxy)-propylamine

Starting from the alcohol 15 (0.27 mmole) and 3-chloropropylamine-hydrochloride (2.7 mmoles), an oily product was obtained.

MS (m/z): 354 (MH⁺).

Example 14

2,8-Dithia-dibenzo[e,h]azulene-1-carbaldehyde

To a dichloromethane solution of the alcohol 15 (3.0 mmoles in 40 ml) dipyridine-chromium-(VI)-oxide (pyridinyl dichromate, PDC, 0.006 mole) was added. The reaction mixture was stirred at room temperature for 18 hours. Diethyl ether (50 ml) was added to the reaction mixture and the thus diluted reaction mixture was purified on a Florisil column to give a yellow crystal product.

$^1$H NMR (ppm, CDCl$_3$): 7.29-7.45 (m, 5H); 7.53-7.56 (m, 1H); 7.65-7.68 (m, 1H); 7.72-7.75 (m, 1H); 7.81 (d, 1H); 9.84 (s, 1H).

The invention claimed is:

1. A compound of the formula I

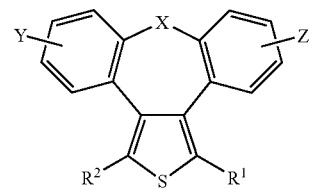

wherein

X is CH$_2$, O, S, S(=O), S(=O)$_2$, or NR$^a$, wherein R$^a$ is hydrogen or a protecting group;

Y and Z are each independently selected from the group consisting of hydrogen, halogen, C$_1$-C$_4$ alkyl, C$_2$-C$_4$ alkenyl, C$_2$-C$_4$ alkynyl, trifluoromethyl, halo-C$_1$-C$_4$ alkyl, hydroxy, C$_1$-C$_4$ alkoxy, trifluoromethoxy, C$_1$-C$_4$ alkanoyl, amino, amino-C$_1$-C$_4$ alkyl, C$_1$-C$_4$ alkylamino, N-(C$_1$-C$_4$-alkyl)amino, N,N-di(C$_1$-C$_4$-alkyl)amino, thiol, C$_1$-C$_4$ alkylthio, C$_1$-C$_4$ alkylsulfonyl, C$_1$-C$_4$ alkylsulfinyl, carboxy, C$_1$-C$_4$ alkoxycarbonyl, cyano, and nitro;

R$^1$ is selected from the group consisting of hydrogen, halogen, C$_1$-C$_7$ alkyl optionally substituted with at least one substituent selected from the group consisting of halogen, hydroxy, C$_1$-C$_4$ alkoxy, thiol, C$_1$-C$_4$ alkylthio, amino, N-(C$_1$-C$_4$) alkylamino, N,N-di(C$_1$-C$_4$-alkyl)-amino, C$_1$-C$_4$ alkylsulfonyl, and C$_1$-C$_4$ alkylsulfinyl; C$_2$-C$_7$ alkenyl optionally substituted with at least one halogen atom; C$_2$-C$_7$ alkynyl: a monocyclic or bicyclic aryl group linked to the rest of the molecule via a direct bond or a C$_1$-C$_4$ alkylene group and optionally substituted with one or two substituents selected from the group consisting of fluoro, chloro, C$_1$-C$_4$ alkyl cyano, nitro, hydroxy, C$_1$-C$_4$ alkoxy; thiol, C$_1$-C$_4$ alkylthio, amino, N-(C$_1$-C$_4$) alkylamino, N,N-di(C$_1$-C$_4$-alkyl)-amino, C$_1$-C$_4$ alkylsulfonyl, and C$_1$-C$_4$ alkylsulfinyl; a monocyclic or bicyclic heteroaryl group linked via a carbon or nitrogen atom to the rest of the molecule via a direct bond or a C$_1$-C$_4$ alkylene group and optionally substituted with one or two substituents selected from the group consisting of fluoro, chloro, C$_1$-C$_4$ alkyl, cyano, nitro, hydroxy, C$_1$-C$_4$ alkoxy, thiol, C$_1$-C$_4$ alkylthio, amino, N-(C$_1$-C$_4$) alkylamino, N,N-di(C$_1$-$_4$-alkyl)-amino, C$_1$-C$_4$ alkylsulfonyl, and C$_1$-C$_4$ alkylsulfinyl; a five-membered or six-membered fully saturated or partly unsaturated heterocycle group linked via a carbon or nitrogen atom to the rest of the molecule via a direct bond or a C$_1$-C$_4$ alkylene group and optionally substituted with one or two substituents selected from the group consisting of fluoro, chloro, C$_1$-C$_4$ alkyl, cyano, nitro, hydroxy, C$_1$-C$_4$ alkoxy, thiol, C$_1$-C$_4$ alkylthio, amino, N-(C$_1$-C$_4$) alkylamino N,N-di(C$_1$-C$_4$-alkyl)-amino, C$_1$-C$_4$ alkylsulfonyl, and C$_1$-C$_4$ alkylsulfinyl; hydroxy, hydroxy-C$_2$-C$_7$ alkenyl, hydroxy-C$_2$-C$_7$ alkynyl, C$_1$-C$_7$ alkoxy, thiol, thio-C$_2$-C$_7$ alkenyl, thio-C$_2$-C$_7$ alkynyl, $C_1$-$C_7$ alkylthio, amino, N-($C_1$-$C_7$ alkyl)amino, N,N-di-($C_1$-$C_7$ alkyl)amino, $C_1$-$C_7$ alkylamino, amino-$C_2$-$C_7$ alkenyl, amino-$C_2$-$C_7$ alkynyl, amino-$C_1$-$C_7$ alkoxy, $C_1$-$C_7$ alkanoyl, aroyl, oxo-$C_1$-$C_7$ alkyl, $C_1$-$C_7$ alkanoyloxy, carboxy, $C_1$-$C_7$ alkyloxycarbonyl or $C_6$-$C_7$ aryloxycarbonyl, carbamoyl, N-($C_1$-$C_7$-alkyl)carbamoyl, N,N-di($C_1$-$C_7$-alkyl)carbamoyl, cyano, cyano-$C_1$-$C_7$ alkyl, $C_1$-$C_7$ alkylsulfonyl, $C_1$-$C_7$ alkylsulfinyl, nitro, and a substituent of the formula II $$(CH_2)_m-Q_1-(CH_2)_n-Q_2-N\begin{matrix}R^3\\R^4\end{matrix} \quad\quad II$$

wherein $R^3$ and $R^4$ are each independently selected from the group consisting of hydrogen, $C_1$-$C_4$ alkyl, and aryl, or $R^3$ and $R^4$ taken together with the nitrogen atom to which they are attached form a heterocycle or heteroaryl group selected from the group consisting of morpholine-4-yl, piperidine-1-yl, pyrrolidine-1-yl, imidazole-1-yl and piperazine-1-yl;

m and n are each independently an integer from 0 to 3;

$Q_1$ and $Q_2$ are each independently selected from the group consisting of oxygen, sulphur, $$-\underset{\underset{y_2}{|}}{\overset{y_1}{C}}- \quad -\underset{}{\overset{y_1}{N}}- \quad -\underset{\underset{H}{|}}{\overset{y_1}{C}}=C- \quad \text{and} \quad -C{\equiv}C-$$

wherein $Y_1$ and $y_2$ are each independently selected from the group consisting of hydrogen, halogen, $C_1$-$C_4$ alkyl optionally substituted with at least one substituent selected from the group consisting of halogen, hydroxy, $C_1$-$C_4$ alkoxy, thiol, $C_1$-$C_4$ alkylthio, amino, N-($C_1$-$C_4$) alkylamino, N,N-di($C_1$-$C_4$-alkyl)-amino, $C_1$-$C_4$ alkylsulfonyl, and $C_1$-$C_4$ alkylsulfinyl; an aryl group optionally substituted with one or two substituents selected from the group consisting of fluoro, chloro, $C_1$-$C_4$ alkyl cyano, nitro, hydroxy, $C_1$-$C_4$ alkoxy, thiol, $C_1$-$C_4$ alkylthio, amino, N-($C_1$-$C_4$) alkylamino, N,N-di($C_1$-$C_4$-alkyl)-amino, $C_1$-$C_4$ alkylsulfonyl, and $C_1$-$C_4$ alkylsulfinyl; hydroxy, $C_1$-$C_4$ alkoxy, $C_1$-$C_4$ alkanoyl, thiol, $C_1$-$C_4$ alkylthio, $C_1$-$C_4$ alkylsulfonyl, $C_1$-$C_4$ alkylsulfinyl, cyano, and nitro; or $y^1$ and $y^2$ taken together with the carbon atom to which they are attached form a carbonyl or imino group;

$R^2$ is hydrogen, carboxy or alkyloxycarbonyl; and pharmaceutically acceptable salts and solvates thereof.

2. The compound of claim 1, or a pharmaceutically acceptable salt thereof, wherein X is S or O.

3. The compound of claim 2, or a pharmaceutically acceptable salt thereof wherein Y and Z are each independently H or Cl.

4. The compound of claim 3 or a pharmaceutically acceptable salt thereof wherein $R^1$ is H, Br, COOH, COOMe or COOEt and $R^2$ is H, COOH, COOMe, or COOEt.

5. The compound of claim 3, or a pharmaceutically acceptable salt thereof, wherein $R^2$ is H and $R^1$ is COOMe, COOEt, or $CH_2OH$.

6. The compound of claim 3 or a pharmacuetically acceptable salt thereof wherein $R^2$ is H and $R^1$ is a substituent having the formula II.

7. The compound of claim 6 or a pharmaceutically acceptable salt thereof, wherein m is 1, n is 1 or 2, $Q_1$ is O, and $Q_2$ is $CH_2$.

8. The compound of claim 7 or a pharmaceutically acceptable salt thereof, wherein $R^3$ and $R^4$ are each independently H or Me.

9. The compound of claim 4 selected from the group consisting of:
 8-oxa-2-thia-dibenzo[e,h]azulene;
 2,8-dithia-dibenzo[e,h,]azulene;
 5-chloro-8-oxa-2-thia-dibenzo[e,h,]azulene;
 8-oxa-2-thia-dibenzo[e,h,]azulene-1, 3-dicarboxylic acid monoethyl ester;
 5-chloro-8-oxa-2-thia-dibenzo[e,h,]azulene-1,3-dicarboxylic acid 1-methyl ester;
 5-chloro-8-oxa-2-thia-dibenzo[e,h,]azulene-1,3-dicarboxylic acid 3-methyl ester; and
 2,8-dithia-dibenzo[e,h,]azulene-1, 3-dicarboxylic acid monoethyl ester.

10. The compound of claim 5 selected from the group consisting of:
 8-oxa-2-thia-dibenzo[e,h,]azulene-1-carboxylic acid ethyl ester;
 5-chloro-8-oxa-2-thia-dibenzo[e,h,]azulene-1-carboxylic acid methyl ester;
 11-chloro-8-oxa-2-thia-dibenzo[e,h,]azulene-1-carboxylic acid methyl ester;
 2,8-dithia-dibenzo[e,h,]azulene-1-carboxylic acid ethyl ester;
 (8-oxa-2-thia-dibenzo[e,h,]azulene-1-yl)-methanol;
 (5-chloro-8-oxa-2-thia-dibenzo[e,h,]azulene-1-yl)-methanol;
 (11-chloro-8-oxa-2-thia-dibenzo[e,h,]azulene-1-yl)-methanol; and
 (2,8-dithia-dibenzo[e,h,]azulene-1-yl)-methanol.

11. The compound of claim 8 selected from the group consisting of:
 dimethyl-[3-(8-oxa-2-thia-dibenzo[e,h,]azulene-1-yl-methoxy)-propyl]-amine;
 dimethyl-[2-(8-oxa-2-thia-dibenzo[e,h,]azulene-1-yl methoxy)-ethyl]-amine;
 3-(8-oxa-2-thia-dibenzo[e,h,]azulene-1-ylmethoxy)-propylamine;
 3-(5-chloro-8-oxa-2-thia-dibenzo[e,h,]azulene-1-yl-methoxy)-propylamine;
 [2-(5-chloro-8-oxa-2-thia-dibenzo[e,h,]azulene-1-yl-methoxy)-ethyl]-dimethyl-amine;
 [3-(5-chloro-8-oxa-2-thia-dibenzo[e,h,]azulene-1-yl-methoxy)-propyl]-dimethyl-amine;
 [2-(11-chloro-8-oxa-2-thia-dibenzo[e,h,]azulene-1-yl-methoxy)-ethyl]-dimethyl-amine;
 3-11-chloro-8-oxa-2-thia-dibenzo[e,h,]azulene1-yl-methoxy)-propylamine;
 [3-(2,8-dithia-dibenzo[e,h,]azulene-1-ylmethoxy)-propyl]-dimethyl-amine;
 [2,8-dithia-dibenzo[e,h,]azulene-1-ylmethoxy)-ethyl]-dimethyl-amine; and
 3-(2,8-dithia-dibenzo[e,h,]azulene-1-ylmethoxy)-propylamine; and a pharmaceutically acceptable salt thereof.

12. A process for the preparation of a compound of the formula I:

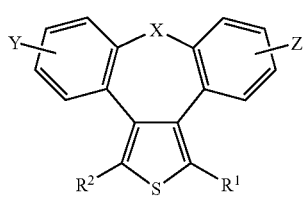

wherein
X is $CH_2$, O, S, $S(=O)$, $S(=O)_2$, or $NR^a$, wherein $R^a$ is hydrogen or a protecting group;

Y and Z are each independently selected from the group consisting of hydrogen, halogen, $C_1$-$C_4$ alkyl, $C_2$-$C_4$ alkenyl, $C_2$-$C_4$ alkynyl, trifluoromethyl, halo-$C_1$-$C_4$ alkyl, hydroxy, $C_1$-$C_4$ alkoxy, trifluoromethoxy, $C_1$-$C_4$ alkanoyl, amino, amino-$C_1$-$C_4$ alkyl $C_1$-$C_4$ alkylamino, N-($C_1$-$C_4$-alkyl)amino, N,N-di($C_1$-$C_4$-alkyl)amino, thiol, $C_1$-$C_4$ alkylthio, $C_1$-$C_4$ alkylsulfonyl, $C_1$-$C_4$ alkylsulfinyl, carboxy, $C_1$-$C_4$ alkoxycarbonyl, cyano, and nitro;

$R^1$ is selected from the group consisting of hydrogen, halogen, $C_1$-$C_7$ alkyl optionally substituted with at least one substituent selected from the group consisting of halogen, hydroxy, $C_1$-$C_4$ alkoxy, thiol, $C_1$-$C_4$ alkylthio, amino, N-($C_1$-$C_4$) alkylamino, N,N-di($C_1$-$C_4$-alkyl)-amino, $C_1$-$C_4$ alkylsulfonyl, and $C_1$-$C_4$ alkylsulfinyl; $C_2$-$C_7$ alkenyl optionally substituted with at least one halogen atom; $C_2$-$C_7$ alkynyl; a monocyclic or bicyclic aryl group linked to the rest of the molecule via a direct bond or a $C_1$-$C_4$ alkylene group and optionally substituted with one or two substituents selected from the group consisting of fluoro, chloro, $C_1$-$C_4$ alkyl cyano, nitro, hydroxy, $C_1$-$C_4$ alkoxy, thiol, $C_1$-$C_4$ alkylthio, amino, N-($C_1$-$C_4$) alkylamino, N,N-di($C_1$-$C_4$-alkyl)-amino, $C_1$-$C_4$ alkylsulfonyl, and $C_1$-$C_4$ alkylsultinyl; a monocyclic or bicyclic heteroaryl group linked via a carbon or nitrogen atom to the rest of the molecule via a direct bond or a $C_1$-$C_4$ alkylene group and optionally substituted with one or two substituents selected from the group consisting of fluoro, chloro, $C_1$-$C_4$ alkyl, cyano, nitro, hydroxy, $C_1$-$C_4$ alkoxy, thiol, $C_1$-$C_4$ alkylthio, amino, N-($C_1$-$C_4$) alkylamino, N,N-di($C_1$-$C_4$-alkyl)-amino, $C_1$-$C_4$ alkylsulfonyl, and $C_1$-$C_4$ alkylsulfinyl; a five-membered or six-membered fully saturated or partly unsaturated heterocycle group linked via a carbon or nitrogen atom to the rest of the molecule via a direct bond or a $C_1$-$C_4$ alkylene group and optionally substituted with one or two substituents selected from the group consisting of fluoro, chloro, $C_1$-$C_4$ alkyl, cyano, nitro, hydroxy, $C_1$-$C_4$ alkoxy, thiol, $C_1$-$C_4$ alkylthio, amino, N-($C_1$-$C_4$) alkylamino , N,N-di($C_1$-$C_4$-alkyl)-amino, $C_1$-$C_4$ alkylsulfonyl, and $C_1$-$C_4$ alkylsulfinyl; hydroxy, hydroxy-$C_2$-$C_7$ alkenyl, hydroxy-$C_2$-$C_7$ alkynyl, $C_1$-$C_7$ alkoxy, thiol, thio-$C_2$-$C_7$ alkenyl, thio-$C_2$-$C_7$ alkynyl, $C_1$-$C_7$ alkylthio, amino, N-($C_1$-$C_7$ alkyl)amino, N,N-di-($C_1$-$C_7$ alkyl)amino, $C_1$-$C_7$ alkylamino, amino-$C_2$-$C_7$ alkenyl, amino-$C_2$-$C_7$ alkynyl, amino-$C_1$-$C_7$ alkoxy, $C_1$-$C_7$ alkanoyl, aroyl, oxo-$C_1$-$C_7$ alkyl, $C_1$-$C_7$ alkanoyloxy, carboxy, $C_1$-$C_7$ alkyloxycarbonyl or $C_6$-$C_7$ aryloxycarbonyl, carbamoyl, N-($C_1$-$C_7$-alkyl)carbamoyl, N,N-di($C_1$-$C_7$-alkyl)carbamoyl, cyano, cyano-$C_1$-$C_7$ alkyl, $C_1$-$C_7$ alkylsulfonyl, $C_1$-$C_7$ alkylsulfinyl, nitro, and a substituent of the formula II

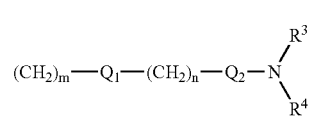

wherein
$R^3$ and $R^4$ are each independently selected from the group consisting of hydrogen, $C_1$-$C_4$ alkyl, and aryl, or $R^3$ and $R^4$ taken together with the nitrogen atom to which they are attached form heterocycle or heteroaryl group selected from the group consisting of morpholine-4-yl, piperidine-1-yl, pyrrolidine-1-yl, imidazole-1-yl and piperazine-1-yl;

m and n are each independently an integer from 0 to 3;

$Q_1$, and $Q_2$ are each independently selected from the group consisting of oxygen, sulphur,

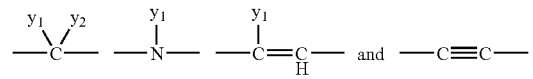

wherein
$Y_1$ and Y2 are each independently selected from the group consisting of hydrogen, halogen, $C_1$-$C_4$ alkyl optionally substituted with at least one substituent selected from the group consisting of halogen, hydroxy, $C_1$-$C_4$ alkoxy, thiol, $C_1$-$C_4$ alkylthio, amino, N-($C_1$-$C_4$) alkylamino, N,N-di($C_1$-$C_4$-alkyl)-amino, $C_1$-$C_4$ alkylsulfonyl, and $C_1$-$C_4$ alkylsulfinyl; an aryl group optionally substituted with one or two substituents selected from the group consisting of fluoro, chloro, $C_1$-$C_4$ alkyl cyano, nitro, hydroxy, $C_1$-$C_4$ alkoxy thiol, $C_1$-$C_4$ alkylthio, amino, N-($C_1$-$C_4$) alkylamino, N,N-di($C_1$-$C_4$-alkyl)-amino, $C_1$-$C_4$ alkylsulfonyl, and $C_1$-$C_4$ alkylsulfinyl; hydroxy, $C_1$-$C_4$ alkoxy, $C_1$-$C_4$ alkanoyl, thiol, $C_1$-$C_4$ alkylthio, $C_1$-$C_4$ alkylsulfonyl, $C_1$-$C_4$ alkylsulfinyl, cyano, and nitro; or $Y_1$ and Y2 taken together with the carbon atom to which they are attached form a carbonyl or imino group;

$R^2$ is hydrogen, carboxy or alkyloxycarbonyl; and pharmaceutically acceptable salts and solvates thereof which comprises one of the following steps (a) through (e):

a) for a compound of the formula I, wherein $R^1$ and $R^2$ are each independently a carboxyl group, cyclizing an α-diketone of the formula III:

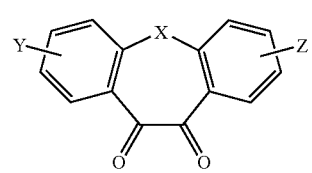

with a compound of the formula IV:

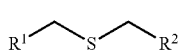

b) for a compound of the formula I, wherein $Q_1$ is —O—, reacting an alcohol of the formula V:

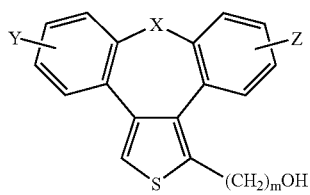

with a compound of the formula VI:

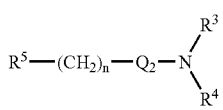

wherein $R^5$ is a leaving group;

c) for a compound of the formula I, wherein $Q_1$ is —O—, —NH—, —S— or —C≡C—, reacting a compound of the formula Va:

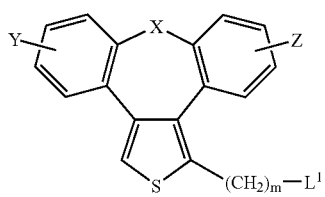

wherein $L^1$ is a leaving group with a compound of the formula VIa:

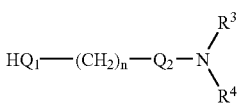

d) for a compound of the formula I, wherein $Q_1$ is —O—, —NH— or —S—, reacting a compound of the formula Vb:

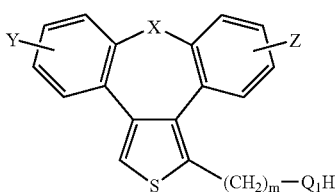

with a compound of the formula VI, wherein $R^5$ is a leaving group; or e) for a compound of the formula I, wherein $Q_1$ is —C=C—, reacting a compound of the formula Vb, wherein $Q_1$ is carbonyl, with a phosphorous ylide.

13. A method of treating inflammation associated with TNF-α comprising administering to a subject an effective amount of a compound according to claim 1.

14. The method of claim 13 wherein the inflammation associated with TNF-α is inflammation associated with rheumatoid arthritis.

\* \* \* \* \*